United States Patent
Wei et al.

(10) Patent No.: US 10,124,117 B2
(45) Date of Patent: Nov. 13, 2018

(54) DRUG DELIVERY DEVICE HAVING CARTRIDGE WITH ENLARGED DISTAL END

(75) Inventors: Min Wei, Morris Plains, NJ (US); Roger W. Groskopf, Saddle Brook, NJ (US); Ruane S. Jeter, Los Angeles, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 883 days.

(21) Appl. No.: 12/990,887

(22) PCT Filed: May 5, 2009

(86) PCT No.: PCT/US2009/042854
§ 371 (c)(1),
(2), (4) Date: Jan. 5, 2011

(87) PCT Pub. No.: WO2009/137486
PCT Pub. Date: Nov. 12, 2009

(65) Prior Publication Data
US 2011/0092917 A1    Apr. 21, 2011

Related U.S. Application Data

(60) Provisional application No. 61/126,433, filed on May 5, 2008.

(51) Int. Cl.
 A61M 5/24 (2006.01)
 A61M 5/32 (2006.01)
 A61M 5/34 (2006.01)

(52) U.S. Cl.
 CPC ............ *A61M 5/24* (2013.01); *A61M 5/2448* (2013.01); *A61M 5/2466* (2013.01);
 (Continued)

(58) Field of Classification Search
 CPC .... A61M 5/24; A61M 5/2455; A61M 5/2466; A61M 2005/2411; A61M 2005/2433;
 (Continued)

(56) References Cited

U.S. PATENT DOCUMENTS 1,803,316 A * 5/1931 Brown .......................... 604/415
2,505,308 A * 4/1950 Smith ..................... A61M 5/24
                                                        206/222

(Continued)

FOREIGN PATENT DOCUMENTS

| EP | 0 701 832 A1 | 3/1996 |
| EP | 0 937 473 A2 | 8/1999 |
| WO | 1990/09202 A1 | 8/1990 |

*Primary Examiner* — Kami A Bosworth
(74) *Attorney, Agent, or Firm* — The Webb Law Firm

(57) ABSTRACT

A drug delivery device is provided herein which includes a tubular body defining an opening. A drug cartridge is also provided having a distal end larger in diameter than the opening. With the drug cartridge being inserted into the tubular body in a use position, the distal end of the drug cartridge is located at least partially externally of the tubular body. The medical pen injector of the subject invention further includes an adaptor engageable with the body. The adaptor encompasses the distal end of the drug cartridge with the drug cartridge being in the use position. The adaptor includes features for mounting a needle assembly thereto. Advantageously, with the subject invention, a drug cartridge having a large distal end may be accommodated with a drug delivery device, e.g., a pen injector type device.

16 Claims, 8 Drawing Sheets

(52) U.S. Cl.
CPC ........... *A61M 5/3202* (2013.01); *A61M 5/347* (2013.01); *A61M 2005/2411* (2013.01)

(58) Field of Classification Search
CPC .. A61M 2005/2437; A61M 2005/2444; A61M 2005/2485; A61M 2005/2488; A61M 2005/2492; A61M 2005/2403; A61M 2005/244; A61M 2005/2474; A61M 2005/2477; A61M 2005/2481
USPC ................................................ 604/240–243
See application file for complete search history.

(56) References Cited

U.S. PATENT DOCUMENTS

| | | | |
|---|---|---|---|
| 3,092,108 A * | 6/1963 | Friedman | A61M 5/24 604/206 |
| 3,115,135 A * | 12/1963 | Sarnoff | A61M 5/24 604/228 |
| 3,131,692 A | 5/1964 | Love | |
| 4,221,218 A * | 9/1980 | Pfleger | A61M 5/28 604/218 |
| 4,731,059 A | 3/1988 | Wanderer et al. | |
| 5,334,162 A | 8/1994 | Harris | |
| 5,549,575 A * | 8/1996 | Giambattista et al. | 604/232 |
| 5,554,134 A * | 9/1996 | Bonnichsen | A61M 5/24 604/232 |
| 5,931,817 A | 8/1999 | Nguyen et al. | |
| 5,989,226 A * | 11/1999 | Hymanson | A61M 5/24 604/110 |
| 6,277,097 B1 * | 8/2001 | Mikkelsen | A61M 5/24 604/187 |
| 7,384,414 B1 * | 6/2008 | Marshall | A61M 5/347 604/198 |
| 2006/0178641 A1 | 8/2006 | Reynolds | |
| 2008/0051729 A1 * | 2/2008 | Cheng | A61M 5/24 604/232 |
| 2008/0097338 A1 * | 4/2008 | Cheng et al. | 604/201 |
| 2009/0192486 A1 * | 7/2009 | Wilmot | A61M 5/2033 604/506 |

* cited by examiner

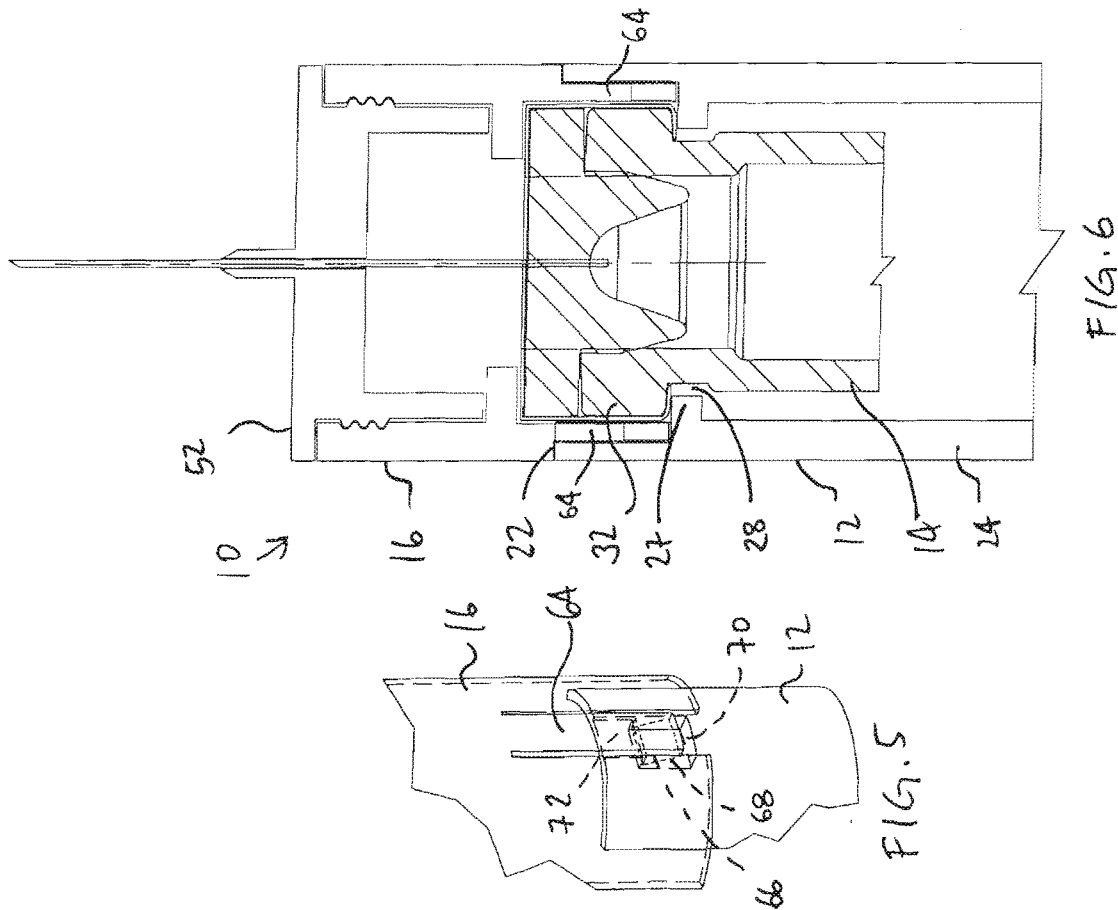
FIG. 5
FIG. 6
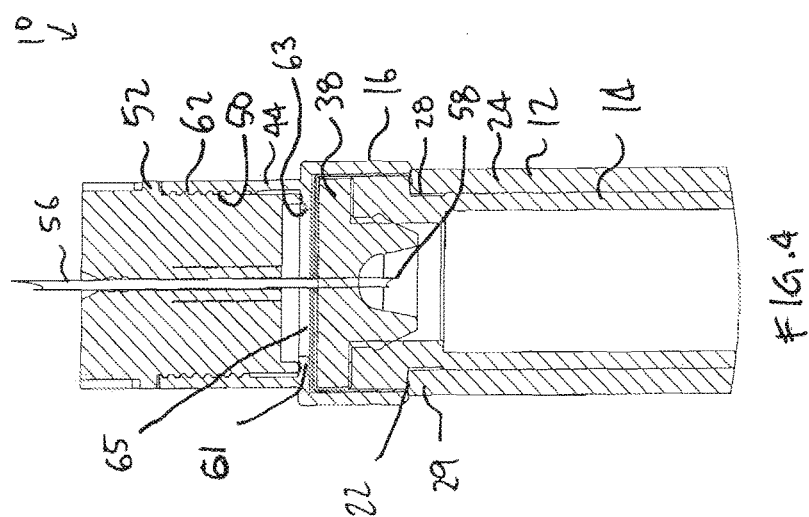
FIG. 4

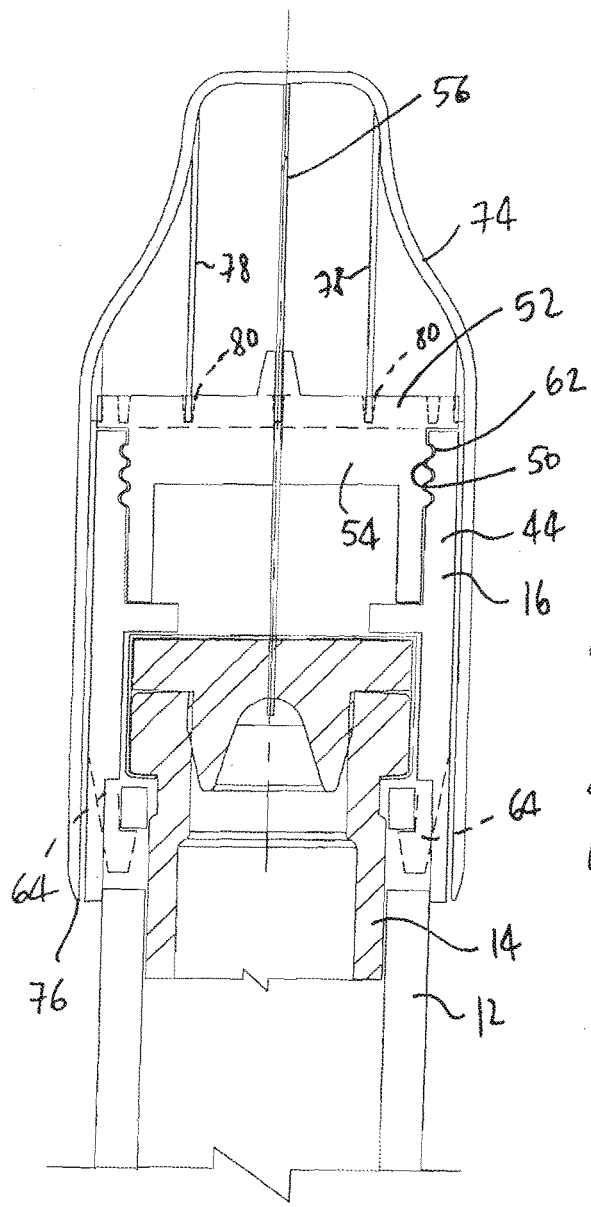
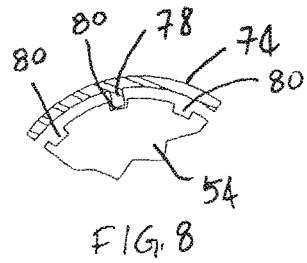
FIG. 8
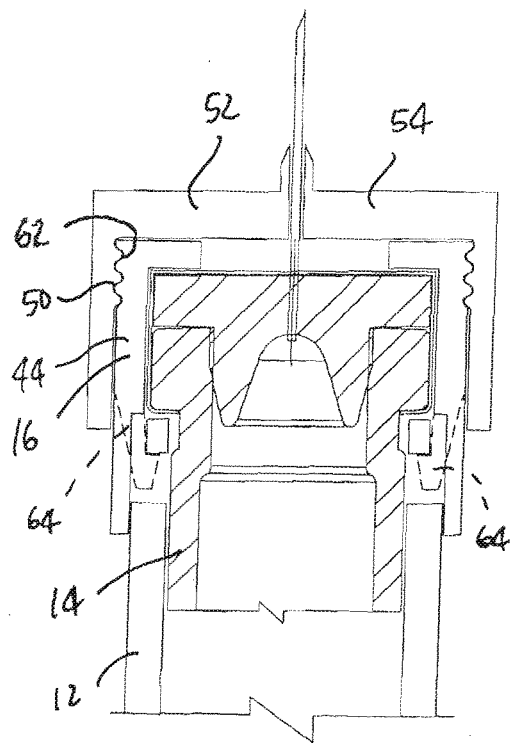
FIG. 7
FIG. 9

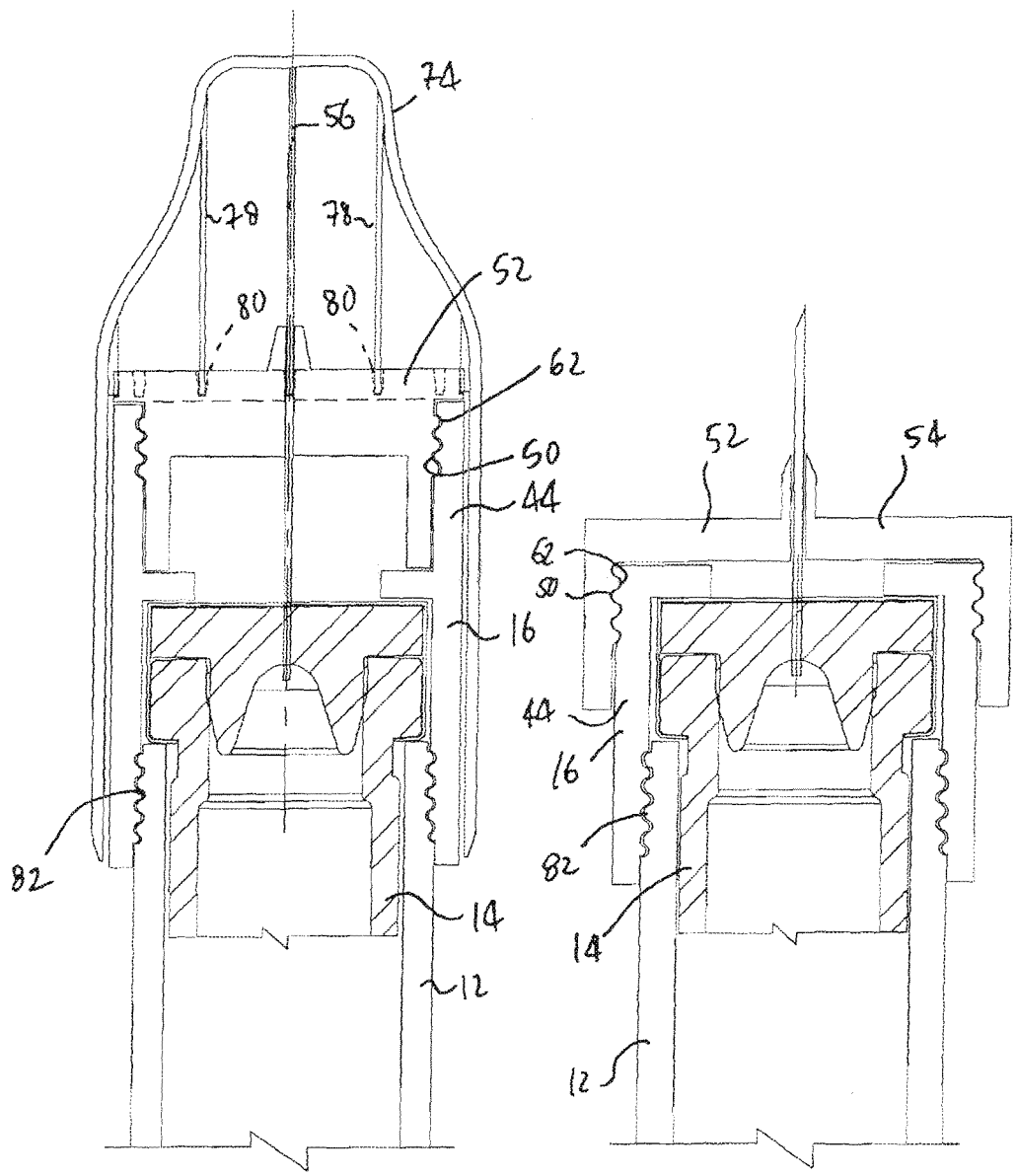

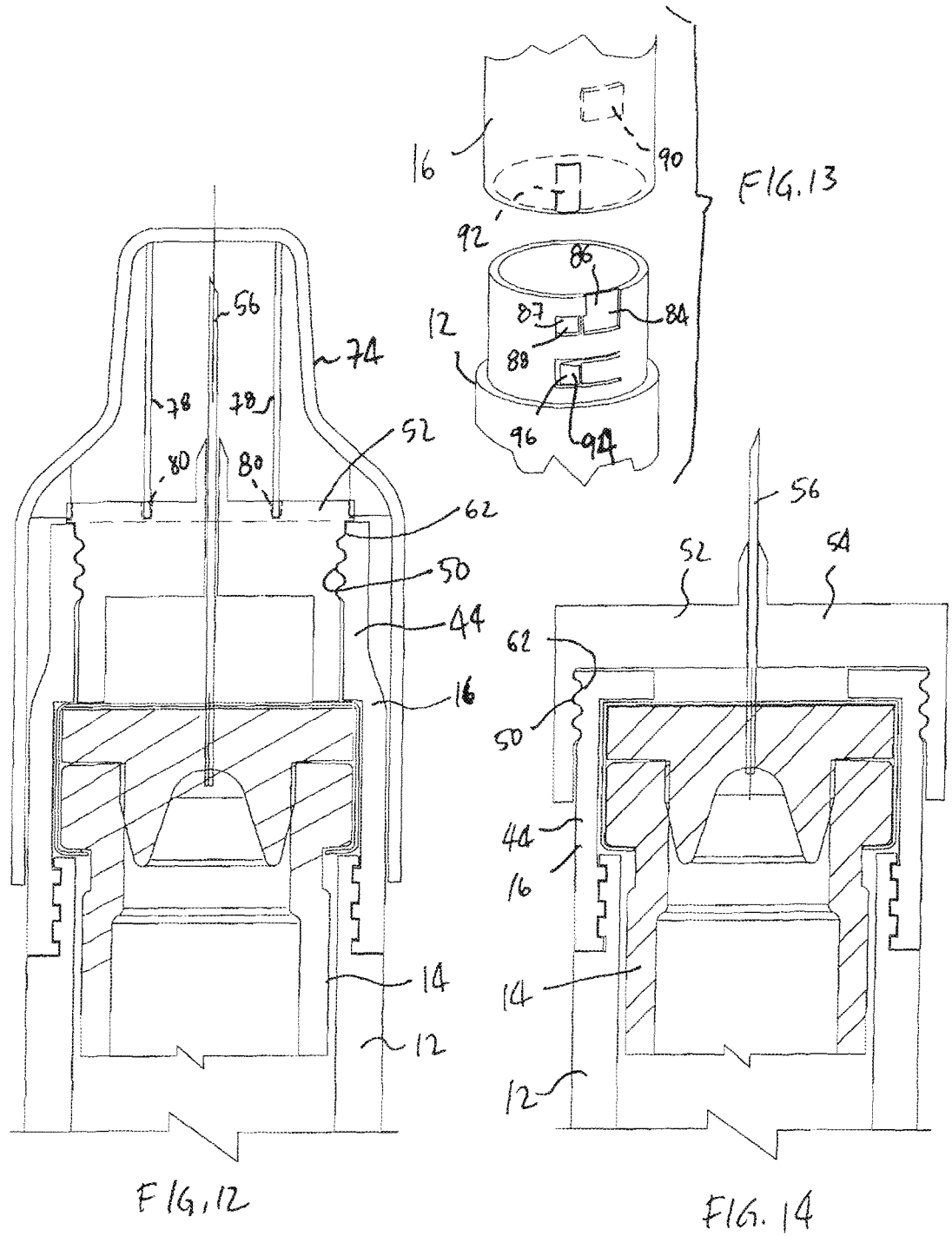

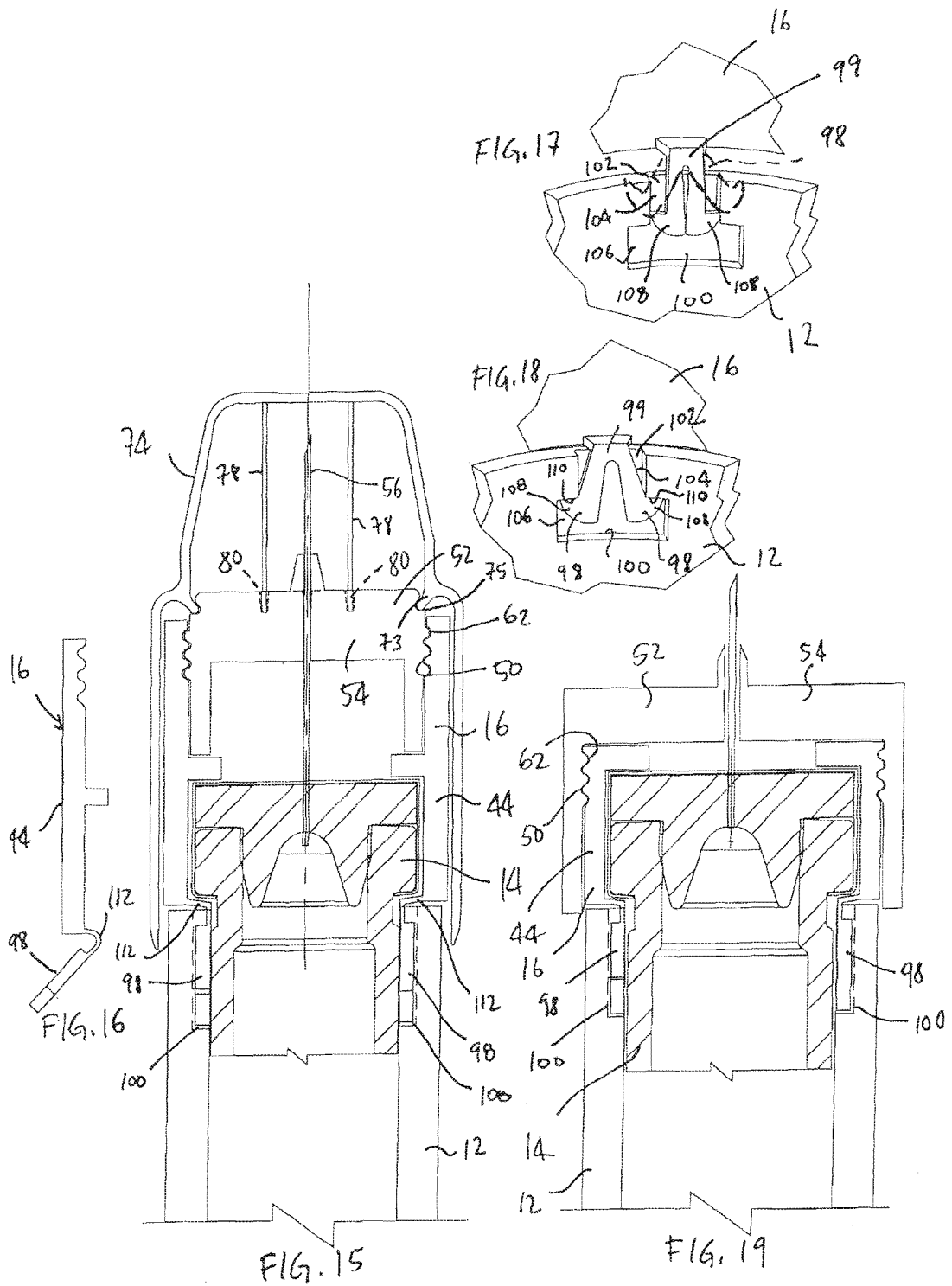

DRUG DELIVERY DEVICE HAVING CARTRIDGE WITH ENLARGED DISTAL END

BACKGROUND OF THE INVENTION

This invention relates to drug delivery devices and, more particularly, to needle-mounting adaptors for drug delivery devices.

Medical pen injectors are well known in the prior art. Pen injectors may have a continuous solid body which houses a cartridge of drug to be administered. This is typically used for single-use pen injectors, where, once a drug cartridge is exhausted, the pen injector is intended for disposal. Re-useable pen injectors are known in the art, such as that shown in U.S. Pat. No. 5,931,817, which is incorporated by reference herein in its entirety. As shown in U.S. Pat. No. 5,931,817, a pen injector may be provided which includes a removable cartridge retainer which can be repeatedly removed to allow for use with multiple drug cartridges. In any regard, drug cartridges are accommodated by pen injectors and are formed to standard sizes, as dictated by ISO specifications (e.g., ISO 11608-3). Thus, with a drug cartridge formed to dimensions outside of the ISO specifications, it may not be accommodated by a standard pen injector.

A need has been developed in the prior art to accommodate a drug cartridge with a larger front end. The front end may be dimensioned so as to be larger than the body of a drug delivery device, such as a medical pen injector, thus preventing full insertion thereinto. A larger front end may be desired to accommodate larger drug volumes or for other considerations, such as manufacturing considerations. A larger front end may permit easier filling, particularly of a powdered or granular substance. With a larger front end, the drug cartridge may extend externally from the body of the drug delivery device. As such, a pen needle can not be mounted onto the body as is known in the prior art.

SUMMARY OF THE INVENTION

A drug delivery device is provided herein which includes a tubular body having a proximal end and a distal end, the tubular body defining an opening at or in proximity to the distal end, the opening defining an inner diameter. A drug cartridge is also provided having a proximal end, a distal end and a barrel portion disposed therebetween. The distal end of the drug cartridge is larger in diameter than the inner diameter of the opening. The drug cartridge is inserted into the tubular body to a use position by first inserting the proximal end of the drug cartridge into the opening. The distal end of the drug cartridge limits insertion of the drug cartridge into the tubular body due to the interengagement of the distal end of the drug cartridge and the tubular body. With the drug cartridge being in the use position, the distal end of the drug cartridge is located at least partially externally of the tubular body. The medical pen injector of the subject invention further includes an adaptor engageable with the body. The adaptor encompasses the distal end of the drug cartridge with the drug cartridge being in the use position. The adaptor includes features for mounting a needle assembly thereto. Advantageously, with the subject invention, a drug cartridge having a large distal end may be accommodated with a drug delivery device, e.g., a pen injector type device.

As used herein, the term "proximal" and derivatives thereof refer to a direction towards the non-patient end of the device (i.e., away from a patient). The term "distal" and derivatives thereof refer to a direction towards the patient end of the device (i.e., towards a patient during an injection).

These and other features of the invention will be better understood through a study of the following detailed description and accompanying drawings.

BRIEF DESCRIPTION OF THE DRAWINGS

FIG. 4 is a partial cross-sectional view taken along line 4-4 of FIG. 1;

FIG. 5 depicts an arrangement for fixing the adaptor useable with the subject invention:

FIG. 6 is a partial cross-sectional view similar to FIG. 4 showing a variation thereto;

FIGS. 7-9 depict the arrangement for fixing the adaptor depicted in FIG. 5 along with needle packaging;

FIGS. 10-11 depict a second arrangement for fixing the adaptor along with needle packaging;

FIGS. 12-14 depict a third arrangement for fixing the adaptor along with needle packaging; and, FIGS. 15-19 depict a fourth arrangement for fixing the adaptor along with needle packaging;

DETAILED DESCRIPTION OF THE INVENTION

Figure 1:
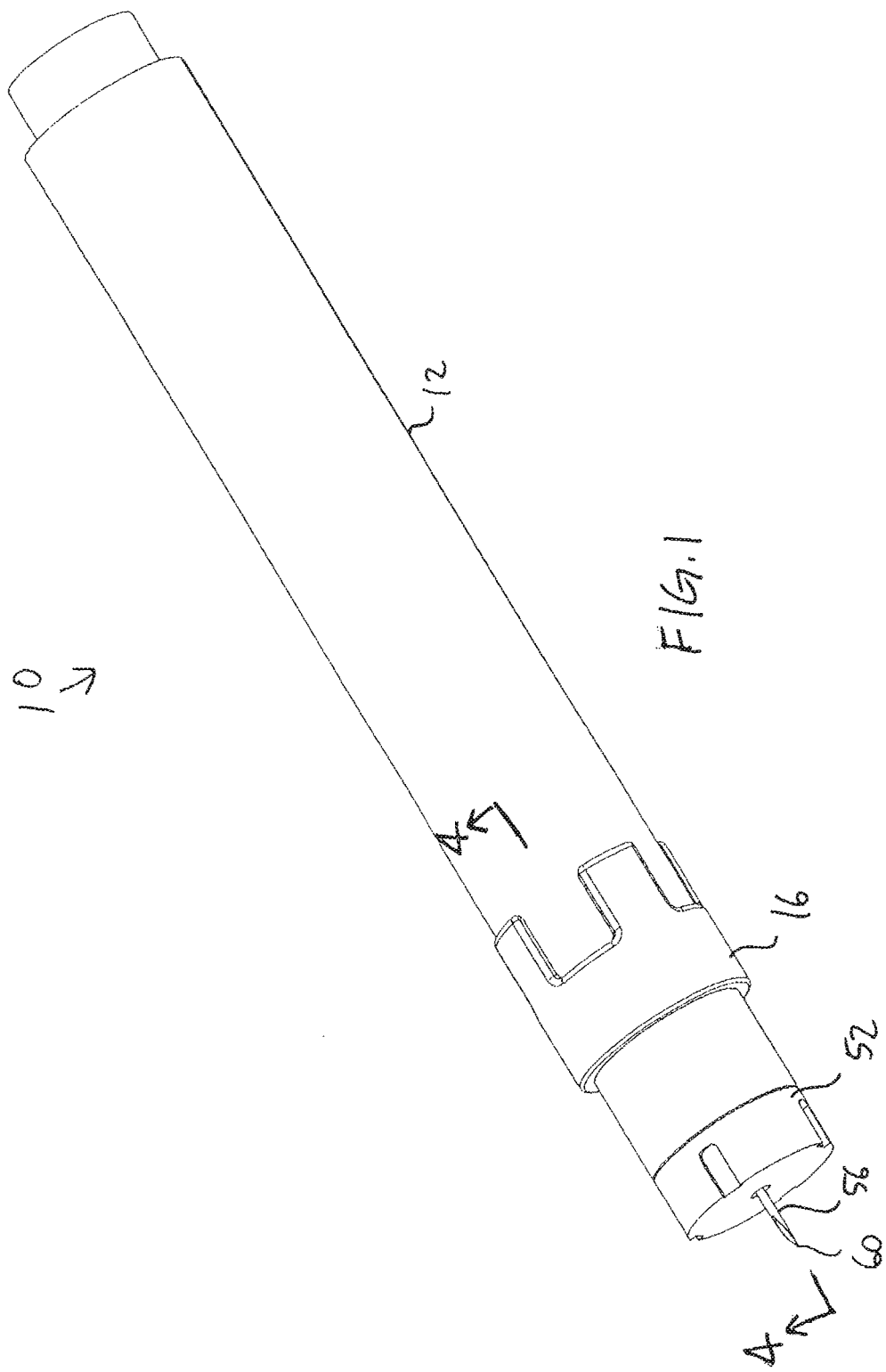
FIG. 1 is a perspective view of a drug delivery device in the form of a medical pen injector formed in accordance with the subject invention.

With reference to FIG. 1, a drug delivery device is depicted. The subject invention may be used with different drug delivery devices, but is particularly well-suited for use with medical pen injectors. For illustrative purposes, a medical pen injector is depicted. The medical pen injector is shown and generally designated with the reference numeral 10. It is to be understood that various types of drug delivery devices may be utilized with the subject invention, including single-use or multiple-use varieties. In addition, fixed dose or set dose devices may be utilized. Further, manually actuated or power driven or power assisted (e.g., spring driven) devices may be utilized. This may include auto-injectors. The medical pen injector 10 is depicted in the figures as a single-use device. The visual depiction of the medical pen injector is for illustrative purposes and is not intended to be limiting. Drug delivery devices compatible with the features described below are useable with the subject invention.

Figure 2:
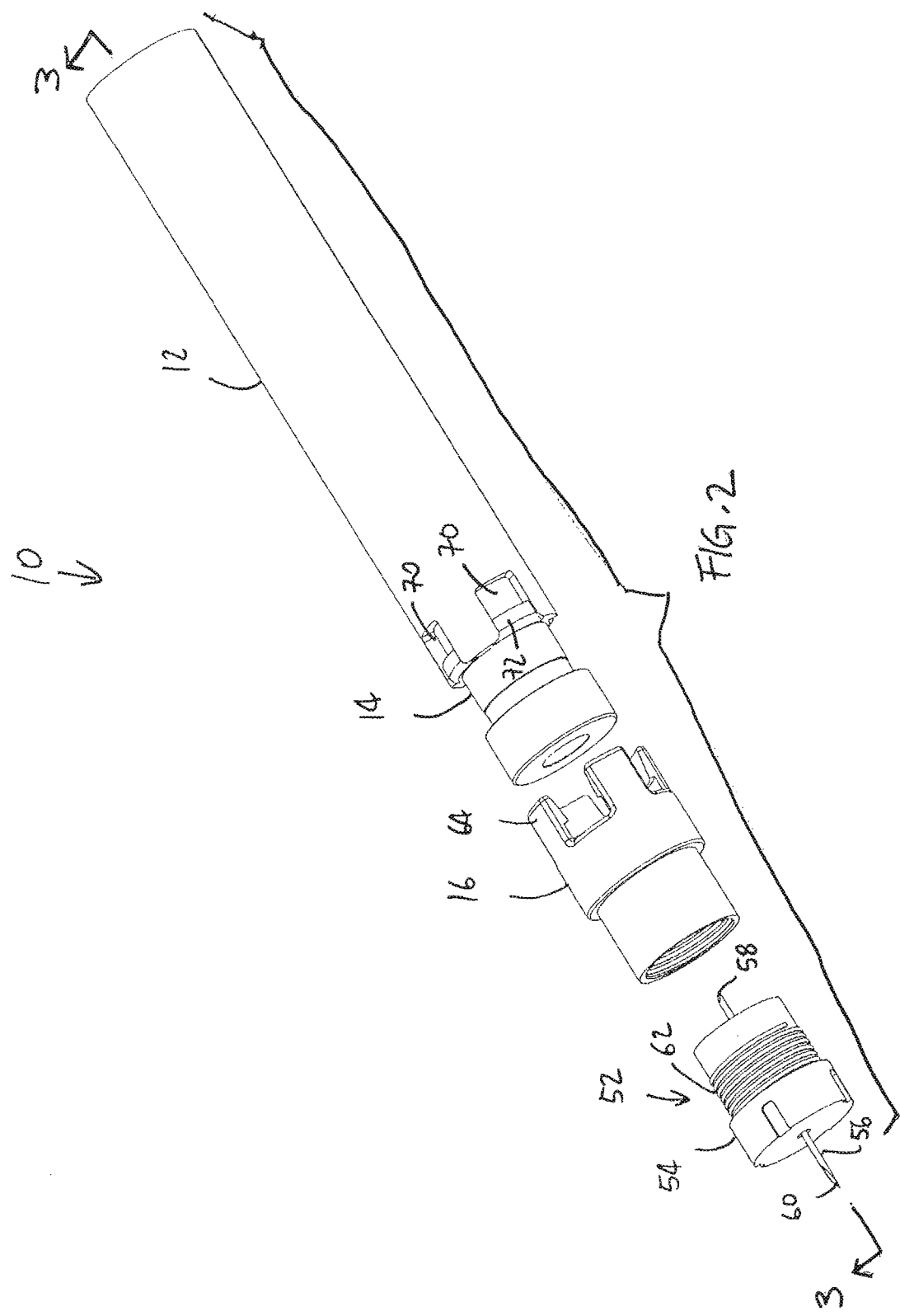
FIG. 2 is an exploded view of the device of FIG. 1.

The medical pen injector 10, as shown in FIG. 2, generally includes a tubular body 12, a drug cartridge 14 and an adaptor 16.

Figure 3:
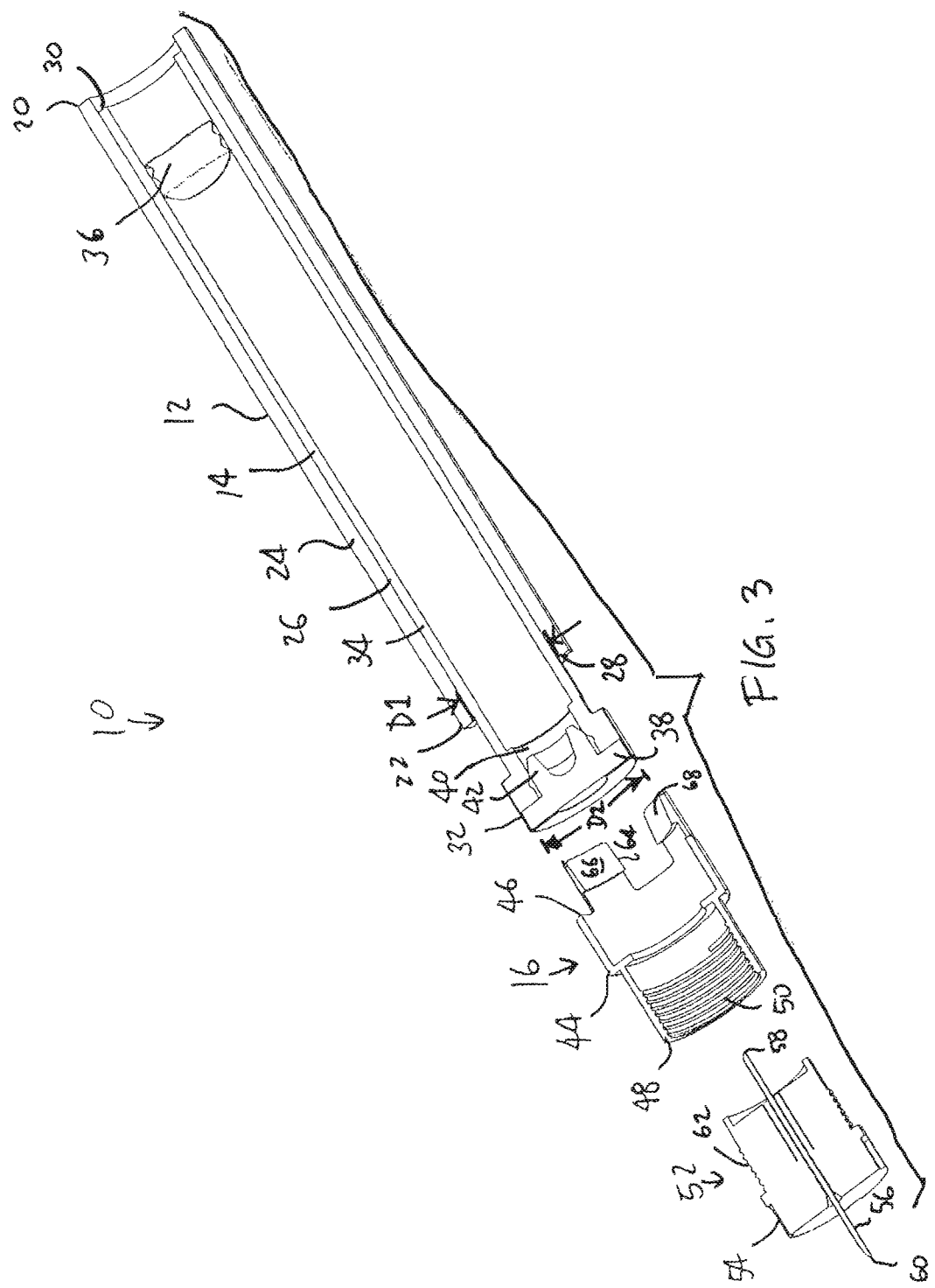
FIG. 3 is a cross-sectional view taken along line 3-3 of FIG. 2.

As best shown in FIG. 3, the tubular body 12 includes a proximal end 20, a distal end 22, and a sidewall 24 which extends between the proximal end 20 and the distal end 22. The sidewall 24 defines a channel 26 between the proximal end 20 and the distal end 22. The tubular body 12 may be the body of the medical pen injector 10 or a component thereof, e.g., a cartridge retainer, such as that shown in U.S. Pat. No. 5,931,817.

The tubular body 12 defines an opening 28 at or in proximity to the distal end 22 having an inner diameter D1. The opening 28 may define a distal terminus of the channel 26. The opening 28 may be defined by a shoulder 27 (FIG. 6) extending inwardly from the sidewall 24, or by a straightwall section 29 of the sidewall 24 (FIG. 4). As shown in FIG. 6, the opening 28 may be formed in proximity to the distal end 22 or at the distal end 22 (FIG. 4). It is preferred that the sidewall 24 have a larger diameter than the diameter D1 extending distally from the opening 28 as discussed below.

The drug cartridge 14 includes a proximal end 30, a distal end 32 and a barrel portion 34 disposed therebetween. The proximal end 30 is open and at least one stopper 36 is slideably disposed in the barrel portion 34 in liquid tight engagement therewith. The distal end 32 is sealed by a septum 38. Drug is contained within the barrel portion 34 between the stopper 36 and the septum 38. As will be appreciated by those skilled in the art, more than one of the stoppers 36 may be provided in defining a multi-chamber drug cartridge. In this manner, the drug cartridge 14 may be configured to permit mixing of multiple components, such as mixing of dry and liquid components to cause reconstitution of a deliverable medicament, and/or to permit sequential delivery of different components. Valving, such as by-pass valving, or other by-pass features (e.g., by-pass channels) may be provided to permit mixing or sequential administration. In addition, or alternatively, the stopper 36 may be configured to permit mixing or sequential administration.

Aperture 40 is defined at or adjacent to the distal end 32 of the drug cartridge 14. The aperture 40 provides access to contents contained within the barrel portion 34. The septum 38 covers the aperture 40. The septum 38 is pierceable by a needle to permit access into the drug cartridge 14. The barrel portion 34 is formed of a rigid material, preferably glass, while the septum 38 is formed of an elastomeric material. The septum 38 may be affixed to the barrel portion 34 using any known technique, such as with an interior seal ring 42 pressed into an interference fit with the aperture 40. Other methods of attaching the septum 38 to the barrel portion 34 may be utilized such as by adhesive, and/or crimping (e.g., with a secondary component). For example, as shown in FIG. 4, a crimped collar 37 may be utilized having an aperture 39 formed therein to permit access to the septum 38. The crimped collar 37 may be metallic (e.g., aluminum) or polymeric material.

As shown in FIG. 3, the distal end 32 of the drug cartridge 14 is formed with an enlarged diameter D2 (i.e., the diameter of the distal end 32 is greater than the diameter of the proximal end 30 of the drug cartridge 14). The enlarged diameter D2 is greater than the inner diameter D1 defined by the opening 28. As such, the enlarged diameter D2 may not pass through the opening 28. The distal end 32 of the drug cartridge 14 may be formed with the enlarged diameter D2 to permit accommodation of a larger volume of drug in the drug cartridge 14 or for other considerations, such as manufacturing considerations or to facilitate filling (e.g., filling with powdered or granular substances). The enlarged diameter D2 is preferably formed about the aperture 40 thus permitting the aperture 40 to be formed with a greater diameter than that provided with an equivalent conventional drug cartridge. The aperture 40, with a larger diameter, permits easier filling of the drug cartridge 14, particularly with dry components (such as powdered or granular substances). The enlarged diameter D2 may be larger than the diameter specified by ISO specifications, such as ISO 11608-3. The tubular body 12, particularly the inner diameter D1 defined at the opening 28, may be formed to accommodate drug cartridges in conformance with ISO specifications. Thus, by providing the drug cartridge 14 with the enlarged diameter D2 outside of the standard specifications, the drug cartridge 14 may not be compatible with standard pen injectors.

With reference to the figures, the adaptor 16 includes a unitary tubular body 44 which extends between proximal end 46 and a distal end 48. Both the proximal end 46 and the distal end 48 are formed open. The adaptor 16 is affixed to the tubular body 12 so as to extend distally from the distal end 22 of the tubular body 12.

As shown in FIG. 4, the drug cartridge 14 is inserted into the tubular body 12 to a use position through the opening 28 with the proximal end 30 of the drug cartridge 14 being first inserted. The distal end 32 of the drug cartridge 14 limits insertion due to the interengagement of the distal end 32 of the drug cartridge 14 and the tubular body 12, particularly about the opening 28. In the use position, the distal end 22 of the drug cartridge 14 is located at least partially externally of the tubular body 12. With the drug cartridge 14 being in the use position and the adaptor 16 being fixed to the tubular body 12, the adaptor 16 encompasses the distal end 32 of the drug cartridge 14. The adaptor 16 secures the drug cartridge 14 in the use position in the tubular body 12.

In addition, the adaptor 16 is formed with needle mounting features 50. The needle mounting features 50 may be threads and/or surface configurations, such as a Luer surface. As shown in FIG. 1, with the adaptor 16 being fixed to the tubular body 12, a needle assembly, e.g., pen needle assembly, 52 may be mounted to the adaptor 16 for use. With the drug delivery device being depicted as a pen injector, the needle assembly is referred to as a pen needle assembly. It is to be understood that other needle assemblies compatible with the invention herein may be utilized. As shown in FIG. 3, the pen needle assembly 52 includes a hub 54 to which is fixed a needle 56 having a proximal end 58 and a distal end 60 formed for insertion into a patient. The hub 54 is formed with needle mounting features 62 formed to cooperate with needle mounting features 50 found on the adaptor 16. As shown in FIG. 4, with the pen needle assembly 52 being mounted to the adaptor 16, the proximal end 58 of the needle 56 is located proximally of the septum 38 so as to access contents within the drug cartridge 14.

With reference to FIG. 4, the adaptor 16 may be formed with a reduced-diameter face 61 which extends inwardly from the tubular body 44. The face 61 may be continuous or discontinuous. The face 61 is disposed to face generally proximally and is shaped and positioned to limit distal movement of the drug cartridge 14 once in the use position. The face 61 terminates at an inner edge 63 that defines a central opening 65. The central opening 65 is shaped and positioned to permit the needle 56 to pass therethrough in accessing the septum 38. The face 61 may be defined on a protrusion and/or at a change in diameter in the adaptor 16.

The adaptor 16 may be fixed to the tubular body 12 in any known manner, including being removably or irremovably mounted. The adaptor 16 may be fixed by cooperating mechanical elements, fusing, and/or adhesive. With reference to FIGS. 2 and 3, in a preferred arrangement, the adaptor 16 is irremovably mounted to the tubular body 12 with one or more locking arms 64 being provided each having a ramped locking detent 66 formed thereon. It is preferred that the locking arms 64 be circumferentially spaced about the proximal end 46 of the adaptor 16, more preferably, evenly spaced. To restrict removability of the adaptor 16, it is preferred that the locking detents 66 be provided with ramped surfaces 68 which are angled so as to converge in a proximal to distal direction. Locking apertures 70 are formed in the tubular body 12 preferably corresponding in quantity to the number of the locking arms 64. The locking apertures 70 may be of limited depth (blind holes) and/or formed through the tubular body 12 (through holes). The locking apertures 70 are shaped to receive in snap engagement the locking detents 66 formed on the locking arms 64. Preferably, a collar 72 is located at the distal end of the locking apertures 70. With the locking detents 66 being received in the locking apertures 70, as shown in FIG. 5, the collar 72 is shaped and positioned to interferingly engage the locking detents 66 upon distal movement of the adaptor 16 relative to the tubular body 12. In this manner, distal movement of the adaptor 16 is restricted. The configuration of the ramped surfaces 68 facilitates the locking detents 66 by-passing the collar 72, upon mounting the adaptor 16 to the tubular body 12, yet resists distal movement of the adaptor 16, as previously described. Optionally, the locking detents 66 may be formed to be releasable with sufficient force being applied thereto; in this manner, the locking detents 66 provide a holding force, rather than a permanent locking force, which may be overcome.

One or more of the locking arms 64 and the locking apertures 70 may be formed on the tubular body 12 and/or the adaptor 16.

In FIGS. 1-4, the locking arms 64 are shown to extend into the locking apertures 70 from outside the sidewall 24. Optionally, one or more of the locking arms 64 may engage the locking apertures 70 from inside the sidewall 24. With this arrangement, preferably, as shown in FIG. 6, the opening 28 may be recessed in the tubular body 12 to be in proximity to the distal end 22 with the sidewall 24 defining a diameter larger than the diameters D1 and D2 between the opening 28 and the distal end 22. Thus, the distal end 32 of the drug cartridge 14 may interengage the tubular body 12 at the opening 28.

With reference to FIG. 7, a packaging 74 may be provided for containing the pen needle assembly 52 prior to use. The packaging 74 is preferably cup-shaped with an open end 76 through which the pen needle assembly 52 may be removed. Advantageously, the pen needle assembly 52 may be maintained in a sterile condition in the packaging 74 prior to use, as is known in the prior art. A rigid or flexible seal (not shown) may be provided to seal the open end 76. The seal is removed to obtain access to the pen needle assembly 52. It is preferred that the packaging 74 be provided with a length greater than the pen needle assembly 52, particularly greater than the length of the needle 56.

As shown in FIG. 7, the pen needle assembly 52 may be contained in the packaging 74 for mounting onto the adaptor 16. Here, the open end 76 must be provided with a sufficient diameter to permit telescoping of the packaging 74 over the adaptor 16. The hub 54 may need to be rotated to mount the needle assembly 52 onto the adaptor 16. To permit rotation of the pen needle assembly 52 with the packaging 74, it is preferred that one or more longitudinally-extending splines 78 be formed on the interior of the packaging 74 sized and located to nest in recesses 80 formed in the hub 54 (FIG. 8). The reverse arrangement may be also utilized. The interengagement of the splines 78 and the recesses 80 permits rotational force applied to the packaging 74 to be transmitted to the hub 54 in causing rotation thereof without relative rotation between the packaging 74 and the hub 54.

Additionally, the interengagement of the splines 78 and the recesses 80 may provide a centering effect on centering the hub 54 within the packaging 74 during storage and prior to use. With reference to FIG. 15, an additional snap member 73, preferably a snap ring, may be provided to seat in a corresponding snap groove 75 formed in the hub 54 to further provide a centering effect.

In addition, reverse rotation causes removal of the pen needle assembly 52 after use. The reverse rotation may be applied directly to the pen needle assembly 52. Preferably, the packaging 74 is placed over the pen needle assembly 52 (as shown in FIG. 7) and reverse rotation is applied to the packaging 74 to remove the pen needle assembly 52. The packaging 74 and the pen needle assembly 52 may be disposed of together. Alternatively, the medical pen injector 10, with the pen needle assembly 52 being mounted thereto, may be disposed of.

As will be appreciated by those skilled in the art, the hub 54 may be mounted to the adaptor 16 in a male or female arrangement. As shown in FIG. 7, the needle mounting features 50 of the adaptor 16 may be formed on an interior portion of the tubular body 44 with the needle mounting features 62 of the pen needle assembly 52 being located on an exterior portion of the hub 54. Alternatively, as shown in FIG. 9, the needle mounting features 50 of the adaptor 16 may be formed on an exterior portion of the tubular body 44 with the hub 54 having the needle mounting features 62 being located on the interior thereof (e.g., the hub 54 may be cup-shaped).

With reference to FIGS. 10-11, the adaptor 16 may be removably fixed to the tubular body 12 with cooperating threads 82 formed thereon. The pen needle assembly 52 may be mounted to the adaptor 16 using the packaging 74 and may be mounted in a male (FIG. 10) or female arrangement (FIG. 11). It is preferred that the cooperating threads 82 have the same thread orientation of any threads used on the pen needle assembly 52. In this manner, mounting of the pen needle assembly 52 onto the adaptor 16 results in tightening of the cooperating threads 82. Also, the adaptor 16 may be mounted to the tubular body 12 in a male or female arrangement. With the use of threads, the adaptor 16 may be removed to allow replacement of the drug cartridge 16.

It is noted that the mounting of the pen needle assembly 52 may require rotation in the same direction as the mounting of the adaptor 16 onto the tubular body 12 with the threads 82. It is desired to prevent unthreading of the threads 82 with the removal of the pen needle assembly 52 after use. To this end, a portion of the packaging 74 may be formed larger to avoid contact with the adaptor 16, particularly during dismounting of the pen needle assembly 52.

With reference to FIGS. 12-14, a bayonet-type lock may be utilized to fix the adaptor 16 to the tubular body 12. With this arrangement, a groove 84 is provided having a first longitudinal portion 86 and a second portion 88 disposed transversely to the first portion 86. A locking protrusion 90 is provided sized and shaped to translate through the groove 84. Preferably, the groove 84 is formed on the tubular body 12 and the locking protrusion 90 is formed on the adaptor 16, although the reverse arrangement may also be utilized. A mixed arrangement can also be utilized where one or more of the grooves 84 and/or the locking protrusions 90 is formed on the adaptor 16 and/or the tubular body 12. With a bayonet-lock-type motion, the locking protrusion 90 is caused to translate along the first longitudinal portion 86 and transversely into the second portion 88. A reverse motion allows for dismounting the adaptor 16 from the tubular body 12.

To permit irreversible locking, a protruding tab 92 may be provided sized and located to traverse a deflectable locking member 94 upon the locking protrusion 90 being seated in the second portion 88 of the groove 84. The locking member 94 may be a cantilevered arm having a tapered head 96 formed to permit one-way movement of the protruding tab 92 thereacross into a locked state. The tapered head 96 resists reversed movement of the protruding tab 92 and thus provides a locking effect. Preferably, the protruding tab 92 is formed on the adaptor 16 and the locking member 94 on the tubular body 12, although the reverse arrangement may also be utilized. A mixed arrangement may be likewise utilized where the one or more of the protruding tabs 92 and/or one or more of the locking members 94 are formed on the adaptor 16 and/or the tubular body 12. Alternatively, the tapered head 96 may be formed to provide resistance against reverse movement of the protruding tab 92 so as to provide a holding force that can be surmounted; the tapered head 96, with sufficient force, can be traversed in allowing for release of the protruding tab 92. Also, a recess or aperture 87 can be formed in the second portion 88 of the groove 84 which can receive the locking protrusion 90 in snap engagement in providing locking or holding force thereto.

With the arrangement of FIGS. 12-14, the pen needle assembly 52 may be mounted to the adaptor 16 using the packaging 74 and may be mounted in a male (FIG. 12) or female arrangement (FIG. 14). Likewise, the adaptor 16 may be mounted to the tubular body 12 in a male or female arrangement.

With reference to FIGS. 15-19, a further arrangement for fixing the adaptor 16 to the tubular body 12 is depicted. In particular, at least one resilient spring finger 98 is provided on the adaptor 16 formed to nest in pockets 100. Preferably, the spring fingers 98 are provided in groupings, such as pairs, having portions which extend in opposing directions, e.g., to define a V-shape. The spring fingers 98 may extend from a base portion 99. As shown in dashed lines in FIG. 17, the spring fingers 98 are extended in unbiased states. The pockets 100 are each formed with an opening 102 having a width less than the spring fingers 98 in the extended, unbiased state. The width of the spring fingers 98 is the width of a single of the spring fingers 98, if provided as such, or the width of the collective grouping (e.g., the width of the pair). As shown in FIG. 17, the spring fingers 98 are provided with sufficient resilience to deflect upon entering the opening 102. The pockets 100 each include a neck 104 which extends from the opening 102 to an enlarged area 106. With the spring fingers 98 being sufficiently inserted into the pockets 100, the spring fingers 98 expand in the enlarged areas 106 to a lock state. The spring fingers 98 (singularly or collectively) have a width greater than the opening 102 in the lock state, although the width may be equal to or less than that of the unbiased state. In the lock state, and upon application of a force trying to withdraw the spring fingers 98, the spring fingers 98 resist reverse motion and limit separation of the adaptor 16 from the tubular body 12. The spring fingers 98 may interengage portions of the tubular body 12 and/or the adaptor 16 surrounding the pockets 100 so as to limit withdrawal of the spring fingers 98 from the pockets 100.

Preferably, to enhance the locking effect of the spring fingers 98, hooks 108 may be provided at the ends of the spring fingers 98. Due to the change in size between the neck 104 and the enlarged area 106, ledges 110 may be defined. Upon force being applied to withdraw the spring fingers 98, the hooks 108 latch against the ledges 110 and resist removal of the spring fingers 98 from the pockets 100.

As shown in FIG. 15, it is preferred that the pockets 100 be formed on interior portions of the tubular body 12. If the adaptor 16 must be formed with a larger diameter than that defined at the pockets 100, a transition 112 may be provided which radially outwardly offsets the tubular body 44 of the adaptor 16 from the pockets 100 (i.e., the tubular body 44 defines a greater diameter than at the pockets 100). The transition 112 may be rigid or may be formed as a living hinge, as shown in FIG. 16, to allow for angular adjustment of the spring fingers 98.

In a preferred arrangement, the spring fingers 98 are formed on the adaptor 16 and the pockets 100 are formed on the tubular body 12. The reverse arrangement may be also utilized, as well as, a mixed arrangement where one or more of the spring fingers 98 are formed on the adaptor 16 and/or the tubular body 12 and one or more of the pockets 100 are formed on the tubular body 12 and/or the adaptor 16.

With the arrangement of FIGS. 15-19, the pen needle assembly 52 may be mounted to the adaptor 16 using the packaging 74 and may be mounted in a male (FIG. 15) or female arrangement (FIG. 19).

As will be appreciated by those skilled in the art, various fixing arrangements may be utilized with the subject invention for fixing the adaptor 16 to the injector body 12. It is preferred that the fixing arrangement not rotate with the pen needle assembly 52 being mounted to the adaptor 16. Although specific arrangements of cooperating mechanical elements are described above, other arrangements compatible with the subject invention may be utilized.

What is claimed is:
1. A drug delivery device comprising:
a tubular body having a proximal end and a distal end, said tubular body including a shoulder extending inwardly from an inner surface of said tubular body, said shoulder defining an opening at or in proximity to said distal end of said tubular body, said opening defining an inner diameter;
a drug cartridge having a proximal end, a distal end and a barrel portion disposed therebetween, said proximal end of said drug cartridge being open, at least one stopper being slideably disposed in said barrel portion, said distal end of said drug cartridge being sealed by a septum, said septum resting on said distal end of said drug cartridge, said distal end of said drug cartridge being larger in diameter than said inner diameter of said opening in said tubular body, wherein, said drug cartridge is inserted into said tubular body to a use position by first inserting said proximal end of said drug cartridge into said opening in said tubular body, said distal end of said drug cartridge limiting insertion of said drug cartridge into said tubular body due to interengagement of said distal end of said drug cartridge and said shoulder of said tubular body; and
an adaptor engageable with said tubular body so as to encompass said distal end of said drug cartridge with said drug cartridge being in said use position and to secure said drug cartridge in said use position in said tubular body, said adaptor including features provided in a first cavity defined by said adaptor for mounting a needle assembly therein,
wherein said adaptor includes a reduced-diameter protrusion defined therein, said reduced-diameter protrusion extending inwardly from an inner surface of said adaptor and between said first cavity and a second cavity defined in said adaptor that encompasses said distal end of said drug cartridge, and defining a diameter smaller than said diameter of said distal end of said drug cartridge, said reduced-diameter protrusion preventing distal movement of said drug cartridge out of said tubular body with said drug cartridge being in said use position.

2. The drug delivery device as in claim 1, wherein said reduced-diameter protrusion defines an opening, said opening in said adaptor providing access to said septum of said drug cartridge.

3. The drug delivery device as in claim 1, wherein said adaptor is removably fixed to said tubular body.

4. The drug delivery device as in claim 1, wherein said adaptor is irremovably fixed to said tubular body.

5. The drug delivery device as in claim 1, wherein said adaptor is fixed to said tubular body by locking detents received in snap engagement in locking apertures.

6. The drug delivery device as in claim 1, wherein said adaptor is fixed to said tubular body by cooperating threads.

7. The drug delivery device as in claim 1, wherein said adaptor is fixed to said tubular body by cooperating elements formed to provide a bayonet-type lock.

8. The drug delivery device as in claim 1, wherein at least one resilient spring finger extends from at least one of said adaptor and said tubular body, and at least one pocket formed to receive said at least one resilient spring finger is formed in at least one of said adaptor and said tubular body, said at least one pocket being formed to allow insertion of said at least one resilient spring finger therein and to prevent removal of said at least one resilient spring finger once fully inserted therein.

9. The drug delivery device as in claim 8, wherein said at least one pocket includes an opening, said opening of said at least one pocket being narrower than said at least one resilient spring finger in an unbiased state, wherein said at least one resilient spring finger is caused to deflect to enter said opening of said at least one pocket.

10. The drug delivery device as in claim 9, wherein said at least one pocket includes an enlarged area, and, wherein, with sufficient insertion of said at least one resilient spring finger into said at least one pocket, said at least one resilient spring finger enters said enlarged area and expands from a deflected state to a lock state, and, wherein, with said at least one resilient spring finger being in said lock state, upon force being applied to remove said at least one resilient spring finger from said at least one pocket, said at least one resilient spring finger interengages with portions of said adaptor or said tubular body surrounding said at least one pocket so as to limit withdrawal of said at least one resilient spring finger from said at least one pocket.

11. The drug delivery device as in claim 8, wherein said at least one resilient spring finger comprises a pair of resilient spring fingers, and wherein said at least one pocket is formed to receive said pair of resilient spring fingers.

12. The drug delivery device as in claim 11, wherein said pair of resilient spring fingers have portions which extend in opposing directions.

13. A drug delivery device assembly comprising:
a tubular body having a proximal end and a distal end, said tubular body including a shoulder extending inwardly from an inner surface of said tubular body, said shoulder defining an opening at or in proximity to said distal end of said tubular body, said opening defining an inner diameter;

a drug cartridge having a proximal end, a distal end and a barrel portion disposed therebetween, said proximal end of said drug cartridge being open, at least one stopper being slideably disposed in said barrel portion, said distal end of said drug cartridge being sealed by a septum, said septum resting on said distal end of said drug cartridge, said distal end of said drug cartridge being larger in diameter than said inner diameter of said opening in said tubular body, wherein, said drug cartridge is inserted into said tubular body to a use position by first inserting said proximal end of said drug cartridge into said opening in said tubular body, said distal end of said drug cartridge limiting insertion of said drug cartridge into said tubular body due to interengagement of said distal end of said drug cartridge and said shoulder of said tubular body;

an adaptor engageable with said tubular body so as to encompass said distal end of said drug cartridge with said drug cartridge being in said use position and to secure said drug cartridge in said use position in said tubular body, said adaptor including features provided in a first cavity defined by said adaptor for mounting a needle assembly therein and a reduced-diameter protrusion extending inwardly from an inner surface of said adaptor and between said first cavity defined in said adaptor and a second cavity defined in said adaptor that encompasses said distal end of said drug cartridge, said reduced-diameter protrusion preventing distal movement of said drug cartridge out of said tubular body with said drug cartridge being in said use position; and a needle assembly having a hub mounted to said features and a needle fixed to said hub, said needle having a proximal end, located proximally of said septum, and a distal end, formed for insertion into a patient.

14. The drug delivery device assembly as in claim 13, wherein said hub is mounted to said adaptor in a male arrangement.

15. The drug delivery device assembly as in claim 13, further comprising a packaging having a cup-shaped body formed to accommodate said needle assembly.

16. The drug delivery device assembly as in claim 15, wherein cooperating elements are formed on said packaging and said hub of said needle assembly to permit rotational force transmitted to said packaging to be transmitted to said needle assembly without relative rotation between said packaging and said needle assembly.

* * * * *